United States Patent [19]

Lyon et al.

[11] Patent Number: 5,549,895
[45] Date of Patent: Aug. 27, 1996

[54] **METHOD AND COLICIN COMPOSITION FOR INHIBITING *ESCHERICHIA COLI* 0157:H7 IN FOOD PRODUCTS**

[75] Inventors: Wanda J. Lyon, Des Moines; Dennis G. Olson; Elsa A. Murano, both of Ames, all of Iowa

[73] Assignee: Iowa State University Research Foundation, Inc., Ames, Iowa

[21] Appl. No.: 62,773

[22] Filed: May 17, 1993

[51] Int. Cl.$^6$ .......................... A61K 35/00; A21D 4/00; A23L 3/34
[52] U.S. Cl. .......................... 424/115; 426/335; 426/532
[58] Field of Search .................................. 426/332, 335, 426/532; 424/115

[56] References Cited

U.S. PATENT DOCUMENTS

| | | |
|---|---|---|
| 4,861,754 | 8/1989 | Farkas-Hinsley .......................... 514/2 |
| 5,043,176 | 8/1991 | Bycroft et al. .......................... 426/335 |

OTHER PUBLICATIONS

Bradley et al, "Colicinogeny of O157:H7 enterohemorrhagic *Escherichia coli* and the shielding of colicin and phage receptors by their O-antigenic side chains" *Canadian Journal of Microbiology* 37:97–104 (1991).
Nielsen J. W. et al, App Environ Microbiol. 56:2142–2145 (1990).
Degnan et al, J. food Protection 55:552–554 (1992).
Hoover D G, Encyclopedia of Microbiology vol. 1:181–190 (1992).
Barnby-Smith F M, Trends in Food Science & Technology 3(6):133–137 (1992)
M. Daeshel, "Antimicrobial Substances from Lactic Acid Bacteria for Use as Food Preservatives", *Food Technology*, 43:164–166 (1989).
*Determinative Bacteriology*, John G. Holt, ed., Williams & Wilkins Company, Baltimore, MD at pp. 100–102 (1977).
H. P. Fleming et al., "Microbial Inhibition by an Isolate of Pediococcus from Cucumber Brines", *Appl. Microbiol.*, 30:1040–1042 (1975).
P. Frederico, "Colicins", *Rev. Belg. Pathol. Med. Exp.*, 29:7–10 (1948).
H. R. Herschman et al., "Purification and Characterization of Colicin E$_2$ and Colicin E$_3$ ", *J. Biol. Chem.* 242:5360 (1967).
J. H. Keene, "Preparation and Chemical Properties of Colicine I", *Canadian J. Microbiol.* 12:425–427 (1966).
U. K. Laemmli, "Cleavage of Structural Proteins during the Assembly of the Head of Bacteriophage T4", *Nature*, 227:680–685 (1970).
O. H. Lowry et al., "Protein Measurement with the Folin Phenol Reagent", *Biol. Chem.*, 193:265–275 (1951).
W. J. Lyon et al., "Partial Purification and Characterization of a Bacteriocin Produced by *Propionibacterium thoenii*", *Appl. Environ. Microbiol.*, 57:701–706 (1991).
W. J. Lyon et al., "Isolation and Purification of Propionicin PLG-1, a Bacteriocin Produced by a Strain of *Propionibacterium theoenii*", *Appl. Envir. Microbiol.*, 59:83–88 (1993).
N. Mermelstein, "Controlling *E. coli* 0157:H7 in Meat", *Food Technol.*, 47:90–91 (1993).
C. R. Merril et al, "Ultrasensitive Strain for Proteins in Polyacrylamide Gels Shows Regional Variation in Cerebrospinal Fluid Proteins", *Science*, 211: 1437–1438 (1981).
R. Nickelson II, "*E. coli* 0157:H7 — A Pathogen of Renewed Concern", *Scope*, 50002:6–7 (1993).
J. R. Tagg et al., "Assay System for Bacteriocins", *Appl. Microbiol.*, 21:943 (1971).

*Primary Examiner*—David M. Naff
*Assistant Examiner*—Sandra Saucier
*Attorney, Agent, or Firm*—Merchant, Gould, Smith, Edell, Welter & Schmidt, P.A.

[57] ABSTRACT

The invention is directed toward strains of *Escherichia coli* which produce a colicin effective in inhibiting the growth of pathogenic Enterobacteriaceae including *E. coli* strain 0157:H7, and the colicin derived from those strains of *E. coli*. The invention also provides methods of using the colicin to inhibit the growth of pathogenic Enteriobacteriaceae in food substances and on hard surfaces.

11 Claims, No Drawings

METHOD AND COLICIN COMPOSITION FOR INHIBITING *ESCHERICHIA COLI* 0157:H7 IN FOOD PRODUCTS

BACKGROUND OF THE INVENTION

Bacteriocins are extracellular proteinaceous antimicrobial substances produced by various species of bacteria that exert a bactericidal activity on the same or closely related species. W. J. Lyon and B. A. Glatz, *Appl. Environ. Microbiol.* 57:701–706 (1991). One of the best studied of the bacteriocins are the colicins produced by *Escherichia coli*. Members of the genus Escherichia are part of the normal flora and almost universal inhabitants of the intestinal tracts of warm-blooded animals and humans. However, some strains of Escherichia are pathogenic and have been implicated in a dysentery-like diarrhea. Enterohemorrhagic *E. coli* are becoming increasingly widespread as food-poisoning agents. These bacteria have caused serious illnesses in the form of copious bloody diarrhea and hemolytic-uremic syndrome. N. Mermelstein, *Food Technol.* 47:90–91 (1993).

The organisms which have been associated with these syndromes are toxin-producing *E. coli* strain 0157:H7. Dairy cattle are considered as a major source of this strain, and *E. coli* O157:H7 has been isolated from bovine feces and raw milk. The organism has also been isolated from retail samples of beef, pork, lamb, chicken and venison. In humans, *E. coli* O157:H7 has caused numerous food-borne illnesses which have recently been associated with improperly cooked ground beef patties. In January, 1993, more than 475 individuals became seriously ill and two individuals died after they consumed undercooked ground beef at restaurants located in several western states in the United States. This incidence was the sixteenth outbreak of food-borne illnesses traced to *E. coli* O157:H7 and the sixth outbreak associated with undercooked ground beef. Consequently, the quality and safety of meat supplies has become a primary concern of both the meat industry and consumers.

Therefore, an object of the invention is to provide a substance which may be used to protect meat and other food products against contamination by *E. coli* O157:H7 and other like pathogenic Enterobacteriaceae. Another object is to provide a method for inhibiting and/or eliminating food pathogens such as *E. coli* O157:H7 in meat and other food products, and on the surfaces of meat processing equipment, and other related apparati such as cutting boards and the like.

SUMMARY OF THE INVENTION

These and other objects are met by the present invention which is directed toward strains of *Escherichia coli* which are capable of producing a colicin effective to inhibit (i.e., retard or eliminate) the growth of a pathogenic bacterium of the family Enterobacteriaceae, and the colicin derived from those strains of *E. coli*. The invention also includes methods of using the colicin derived from those strains to inhibit the growth of pathogenic Enterobacteriaceae in food substances and on hard surfaces. The invention also provides a composition containing the colicin which may be formulated, for example, as a spray for use as a sanitizing wash of, for example, bovine carcasses during the evisceration process.

The present invention provides strains of *E. coli* which are capable of producing different colicins which are effective in inhibiting the growth of *Escherichia coli* strain O157:H7 or a variant thereof, and/or other pathogenic, Gram-negative Enterobacteriaceae including, for example, Shigella spp., Salmonella spp., and other Escherichia spp. Examples of colicin-producing strains of *E. coli* according to the invention, include *E. coli* isolate ECL1, *E. coli* isolate ECL6, *E. coli* isolate ECL8, and *E. coli* isolate ECL12.

The invention also provides a substantially pure colicin derived from the foregoing colicin-producing strains of *E. coli*. As used herein, the term "substantially pure" means that the colicin has been extracted and isolated from its natural association with other substances and elements of the bacteria, using conventional procedures to isolate proteins from bacterial association.

It is preferred that the colicin of interest is capable of inhibiting the growth of one or more species and/or strains of pathogenic Enterobacteriaceae, as for example, Shigella spp. such as Shigella dysenteriae, *Shigella flexneri*, *Shigella boydii*, *Shigella sonnei*, and the like; Salmonella spp. such as *Salmonella typhi*, *Salmonella typhimurium*, *salmonella paratyphi A*, *Salmonella choleraesuis*, and the like; Escherichia spp. such as *Escherichia coli* strain O157:H7, *Escherichia freundii*, and the like; and Enterococcus spp. It is most preferred that the colicin is capable of inhibiting the growth of *Escherichia coli* strain O157:H7.

The colicin may be applied to meats and other food products, and/or onto hard surfaces such as the surfaces of meat processing equipment and other related apparati such as a cutting board, to inhibit the growth of pathogenic organisms. The colicin may be formulated into a composition containing the colicin in an amount effective to inhibit the growth of a pathogenic Enterobacteriaceae, preferably *Escherichia coli* strain O157:H7, in admixture with a non-toxic, biocompatible carrier. The colicin may be formulated as a liquid composition using an aqueous medium such as water, or as a dry form such as a freeze-dried, powder, and the like. The liquid may be prepared as a concentrate which may be later diluted as desired. The liquid composition may be provided in combination with a commercially available means for spraying the composition on the food product or hard surface. Preferably, the liquid composition contains the colicin in an amount of from about 500 to about 1500 arbitrary units (AU)/ml, preferably from about 800 to about 1200 AU/ml, preferably from about 900 to about 1100 AU/ml, most preferably about 1000 AU/ml. The term "arbitrary units" (AU), as used herein, means the anti-microbial activity of the colicin defined as the reciprocal of the highest dilution causing complete inhibition of an indicator lawn.

The composition may further include an effective amount of a sanitizing agent to cooperate with the colicin and enhance the bactericidic action of the composition, as for example a water-soluble chloride source such as a minor but effective amount of a household chlorine bleach. Other sanitizing agents useful in the present compositions include, for example, organic acids such as lactic acid, acetic acid, and the like. Preferably, the composition includes from about 0.1 to about 1 ppm of a sanitizing agent, preferably from about 0.2 to about 0.8 ppm, preferably from about 0.4 to about 0.6 ppm. The composition may further include other additive agents as desired, as for example, stabilizers, extenders, preservatives, and the like.

The invention also provides a method for inhibiting the growth of a pathogenic Enterobacteriaceae on and/or in a food product. The method includes applying to the surface of a food substance, an effective amount of a colicin derived from a colicin-producing strain of *Escherichia coli* to inhibit the growth of the pathogenic bacterium. In a preferred method, the colicin is derived from *Escherichia coli* strain ECL1, *E. coli* ECL6, *E. coli* ECL8, and *E. coli* ECL12.

Colicins are a naturally occurring proteinaceous antimicrobial substance, and are considered to be substantially non-toxic substances. Use of colicins in foods such as meats would be in accordance with the current FDA guidelines for the use of bacteriocins in foods. The colicin is preferably combined with an aqueous carrier to form a solution which may then be sprayed or poured onto the surface of the food substance. The colicin may also be in a dry form such as a powder.

Preferably, the colicin is applied to the food substance in an amount of from about 5,000 to about 15,000 AU/gm, preferably from about 7,500 to about 12,500 AU/gm, preferably from about 9,000 to about 11,000 AU/gm, most preferably about 10,000 AU/gm. The colicin may be applied, for example, on the surface of an animal carcass such as a side of beef and other like skinned meat portion, which may then be further processed, for example, by grinding or dicing to admix the colicin throughout the mass of the resulting processed meat. The colicin may also be applied to the surface of a ground meat such as ground beef and admixed with the meat. Preferably, the colicin-containing food product is maintained at a temperature of from about 4° to about 10° C. until use.

Also provided according to the invention is a food product made of an edible food substance in combination with an effective amount of the colicin to inhibit the growth of *Escherichia coli* strain O157:H7 and/or other pathogenic strains of Enterobacteriaceae in the food mixture. The edible food substance may be in the form of an animal carcass or portion thereof (i.e., leg of lamb, steak cut, and the like), fish, seafood, a ground meat, a processed meat such as a beef stick, sausage, bologna, frankfurter, a cured meat such as ham, and the like.

A composition containing the colicin may also be applied to a hard surface to sanitize the surface and eliminate bacterial contaminants. The composition may be applied, for example, to the surface of all or part of a meat grinding apparatus, a mixer, a cutting apparatus, and other like meat processing apparati; surfaces such as human skin (i.e., hands), gloves, and the like; and other like surfaces. An effective amount of the colicin is applied onto the hard surface to inhibit the growth of *Escherichia coli* strain O157:H7 and/or other pathogenic Enterobacteriaceae thereon.

Advantageously, the present invention provides a colicin useful for inhibiting the growth of *E. coli* strain O157:H7 in food substances, including the surfaces of meat products such as sides of beef and the like, ground meats, processed meats such as sausage, and the like.

DETAILED DESCRIPTION OF THE INVENTION

EXAMPLE I

Isolation and Growth of Colicin-Producing Enterobacteriaceae

I. Isolation of Colicin-Producing Strains from Fecal Material.

Colicin-producing strains of bacteria were isolated according to the method described by Pierre Fredericq, "Colicins," pages 7 to 10 (19__). Briefly, trypticase soy broth was inoculated with a sample of feces from obtained from swine fecal runoff, and refrigerated at 37° C. overnight. Other sources may also be used including human and other animal feces. A $10^{-5}$ to $10^{-7}$ dilution of the culture (1 ml.) was seeded onto a plate of a nutrient agar. A second layer of 5 ml of agar was poured over the first layer, and the plate was incubated for 24 hours. The seeded culture was developed as isolated colonies between the two layers of agar. *Escherichia coli* strain O157:H7 was used as the indicator strain for colicin activity. The sterile surface of the upper layer was seeded evenly with *Escherichia coli* strain O157:H7. After 24 hours at 37° C., the indicator strain developed uniformly, except for circular inhibition zones centered in the depth by active colonies, which were then picked from the plate using standard techniques.

II. Characterization of Isolated Strains.

The isolated strains were analyzed to provide a profile of biochemical reactions according to standard techniques, as described, for example in A. L. Smith, *Determinative Bacteriology*, at pages 100–102, The Williams & Wilkins Company, Baltimore, Md. (1977). Based on these characteristics, the strains were classified as strains of *Escherichia coli* with the following strain identification numbers: *E. coli* isolate ECL1, *E. coli* isolate ECL6, *E. coli* isolate ECL8, and *E. coli* isolate ECL12.

The individual strains were different from each other by their ability to inhibit *E. coli* O157:H7, *E. coli* α-DH5, *E. coli* V517, and *Salmonella typhimurium* as shown in the table below (+=inhibition; ±=some inhibition; —=no inhibition; degree of inhibition=++++ (greatest) to=(least)). *E. coli* O157:H7 was obtained from American Type Culture Collection (ATCC). The remaining three indicator strains were from the Department of Microbiology, Immunology and Preventive Medicine, Iowa State University, Ames, Iowa *E. coli* strains ECL1, ECL6, ECL8 and ECL12 have been placed on deposit with ATCC on Jul. 29, 1993, under ATCC accession Nos. 69373, 69374, 69375 and 69376, respectively.

| *E. coli* Isolate | *E. coli* O157:H7 | *E. coli* α-DH5 | *E. coli* V517 | *Salmonella typhimurium* |
| --- | --- | --- | --- | --- |
| ECL1 | ++++ | ++++ | +++ | +++ |
| ECL6 | +++ | ++++ | ++ | ++ |
| ECL8 | ++ | ++ | ++ | + |
| ECL12 | + | +++ | ++ | +/− |

The zone of inhibition against *E. coli* O157:H7 was more marked in Isolate strain ECL1 than Isolate strain ECL6, which indicates that the colicins produced by these isolates are different from each other. Strains ECL8 and ECL12 were less effective in inhibiting *E. coli* O157:H7 than strains ECL1 and ECL6. *Salmonella typhimurium* was inhibited by all *E. coli* isolates, however, the degree of inhibition was variable which indicates that each of the colicin are distinct and different from each other.

III. Growth and induction of *E. coli* Isolates ECL1.

The *E. coli* isolate strain ECL1 was grown and induced according to the method of H. R. Herschman and D. R. Helinski, *J. Biol. Chem.* 242: 5360 (1967). In brief, a sterile M-9 Casamino acids media was prepared by combining the following ingredients in 4-liters distilled water.

| | |
| --- | --- |
| Na$_2$HPO$_4$ | 6 gm |
| KH$_2$PO$_4$ | 3 gm |
| NH$_4$Cl | 1 gm |
| NaCl | 0.5 gm |

-continued

| | |
|---|---|
| CaCl$_2$ | 5 gm |
| MgSO$_4$.H$_2$O (1M) | 1 ml |
| glucose, 40% | 1 ml |
| casamino acids, 20% | 1 ml |

The prepared media (4 L) was inoculated with *E. coli* isolate ECL1, and grown with agitation at 37° C. to a late log phase. The culture was used to inoculate 100 liters, sterile M-9 Casamino acids medium which had been equilibrated at 37° C. Sufficient inoculum was added to provide an initial cell concentration to $2 \times 10^7$ cells per ml. The culture was vigorously aerated, and allowed to grow to about $5 \times 10^4$ cells per ml with the fermenter agitation control set at 250 rpm (about 3 hours of incubation). About 0.2 mg/l Mitomycin C was added. The induction process was continued with aeration and the fermenter agitation set at 250 rpm.

After a 2 hour induction period, the culture sample was removed and the induced cells were then harvested.

The remaining three *E. coli* isolates (ECL6, ECL8, ECL12) may also be grown and induced by this process.

EXAMPLE II

Purification of Colicins

The colicin from the *E. coli* isolate ECL1 was purified according to a standard protein purification method by salt extraction, ammonium sulfate precipitation, and ion exchange chromatography, as described by H. R. Herschman and D. R. Helinski, *J. Biol. Chem.* 242:5360 (1967).

Purification was carried out at 0°–4° C. The standard potassium buffer was 0.01M, pH 7.

I. Extraction of colicin activity.

Although the colicins are extracellular, over 90% of the activity of the colicins may sediment out with the cell pellet following induction. Therefore, it is important to remove colicin activity from the surface of the cell without lysing the bacteria. Accordingly, the packed cells were successively washed with 1.0M NaCl in standard potassium phosphate buffer (0.01M, pH 7) to solubilize about 40% of cell-bound colicin activity, without cell lysis.

The cell pellet from the 100-liter induced culture of *E. coli* ECL1 was extracted for 30 minutes in a Waring Blender at low speed with 333 ml of 1.0M NaCl in standard potassium phosphate buffer. After extraction, the cell suspension was centrifuged for 10 minutes at 5000×g. The supernatant was decanted and saved. Extraction of the cell pellet was repeated twice, and the three extracts were pooled.

The cell pellet from a 50-liter induced culture *E. coli* ECL1 was extracted in a similar fashion in the Waring Blender with four 250-ml portions of 1.0M NaCl in standard potassium phosphate buffer. The colicin-containing supernatants were pooled for subsequent purification.

II. Ammonium Sulfate Fractionation of Colicin.

The volume of the pooled colicin extracts from *E. coli* ECL1 was adjusted to 1 liter with the above-described sodium chloride extraction buffer. Solid ammonium sulfate, 114 g, was added slowly to the crude colicin extract, with constant stirring at 4° C. The suspensions was further stirred for 30 minutes and then centrifuged at 26,000×g for 30 minutes. The precipitate was discarded and the supernatants was returned to the cold bath for precipitation of colicin activity.

The majority of colicin activity (about 60 to 90%) precipitated between 20% to 40% ammonium sulfate saturation. An additional 129 g of ammonium sulfate was slowly added to the colicin preparation and the suspension was stirred for 30 minutes at 4° C. The suspension was then centrifuged again at 26,000×g, the supernatant was discarded, and the ammonium sulfate pellet was resuspended in 50 to 70 ml of standard potassium phosphate buffer. The colicin suspension was dialyzed for 18 hours against 4 liters of standard potassium phosphate buffer. The colicin suspension was freeze-dried into a powder, and stored at −80° C. until needed.

III. DEAE-Sephadex Chromatography.

The colicin preparation from *E. coli* ECL1 was resuspended in standard potassium phosphate buffer and applied to a DEAE-Sephadex A-50 column, 4×50 cm, prepared in standard potassium phosphate buffer, and washed with two 10-ml rinses of the same buffer. The colicin was eluted from the column with a 1400-ml linear gradient of 0.0 to 0.5M NaCl in standard potassium phosphate buffer. Fractions of 10 ml were collected and monitored for absorbance and colicin activity. Fractions containing high specific activities were combined and dialyzed overnight against distilled water in a continuous flow dialyzer, and lyophilized.

EXAMPLE III

Characterization of Colicins

The purified colicins may be characterized by standard techniques known and used in the art, including polyacrylamide gel electrophoresis, ultracentrifugal characterization, ion exchange chromatography and isoelectric focusing electrophoresis. See, for example, H. R. Herschman and D. R. Helinski, *J. Biol. Chem.* 242:5360 (1967); and W. J. Lyon and B. A. Glatz, *Appl. Envir. Microbiol.* 59:83–88 (1993).

I. Rotofor isoelectric focusing.

A Rotofor isoelectric focusing chamber (Bio-Rad) may be used as a final purification technique. Colicin eluded from ion exchange columns is assayed for colicin activity by the critical dilution method.

The Rotofor cell is prefocused with 40 ml of 5% glycerol in distilled water containing 2% (vol/vol) Rio-Lyte ampholytes (1:1 ratio of pH 3 to 10 and pH 3 to 7; Bio-Rad), 1 mM EDTA, and 100 mM KCl with 12 W of constant power at 4° C. for 1 hour to establish the pH gradient.

After the Rotofor cell is prefocused, the colicin sample is injected near the middle of the focusing chamber; the sample is focused for another 3 hours. Twenty 1.5-ml fractions are harvested as described by the manufacturer of the cell, and the pH values of the fractions are measured. Ampholytes are removed by dialyzing (Spectra-Por no. 3 dialysis tubing) against 100 volumes of 1M NaCl containing 1 mM EDTA and 1 mM phenylmethylsulfonyl fluoride. Individual fractions are assayed for colicin activity by the critical dilution method as described by C. R. Merril et al, *Science* 211:1437–1438 (1981). The fraction containing activity is analyzed on a 20% continuous sodium dodecyl sulfate-polyacrylamide gel as described hereinbelow.

II. SDS-PAGE.

Polyacrylamide gel in the presence of 0.1% SDS is performed according to the method of U. K. Laemmli, *Nature* 227:680–685 (1970). The polyacrylamide and N,N'-methylenebisacrylamide (Sigma) concentrations are 5 and 0.15%, respectively, in the stacking gel (1 ml) and 18 and 0.5%, respectively, in the separating gel (10 ml). The gels are stained with Silver stain (Sigma) according to the method of C. R. Merril et al, *Science* 211:1437–1438 (1981). The colicin protein band is compared to the mobility of protein standards on the gel, and the molecular weight of the colicin is determined by its $R_f$ value. Protein standards and their molecular weights are as follows: ovalbumin 43,000; carbonic anhydrase, 29,000; β-lactoglobulin, 18,400; lysozyme, 14,300; bovine trypsin inhibitor 6,200; α- and β-insulin, 3,000 (Bethesda Research Laboratories, Gaithersburg, Md.).

III. Protein Determination.

Colicin concentrations are determined by a modification of the method of O. H. Lowry et al., *Biol. Chem.* 193:265–275 (1951), according to the specifications of the manufacturer of the reagents (Sigma).

IV. Measurement of Activity of Purified Colicin Preparation.

Antimicrobial activity of the producer strain may be measured by an agar spot assay according to the method of H. P. Fleming et al., *Appl. Microbiol.* 30:1040–1042 (1975). Activities of the colicin preparations may be measured by the critical dilution method as described by A. Mayr-Harting et al., in *Methods in Microbiology (vol. 7A)*, pages 315–422, J. R. Norris and D. W. Ribbons (ed.), Academic Press, Inc., New York N.Y. (1972); J. R. Tagg et al., *Appl. Microbiol.* 21:943 (1971); and W. J. Lyon and B. A. Glatz, *Appl. Envir. Microbiol.* 59:83–88 (1993). Antimicrobial activity of the colicin is defined as the reciprocal of the highest dilution causing complete inhibition of the indicator lawn and is expressed as "arbitrary units" (AU) per milliliters.

In brief, the colicin activity is measured by adding 5 μl of purified colicin spotted onto sensitive cell lawns prepared according to the method described by W. J. Lyon and B. A. Glatz, *Appl. Environ. Microbiol.* 57:701–706 (1991); and W. J. Lyon and B. A. Glatz, *Appl. Environ. Microbiol.* 59:83–88 (1992). About $10^7$ cells of indicator organisms are added to soft agar overlays, and plates incubated as appropriate for the indicator organism (i.e., 37° C.) for 18 hours. The clear zones of inhibition and their respective concentrations of colicin are noted. The assays are performed in duplicate, and the results presented as the means of duplicate trials.

EXAMPLE IV

Inhibition of *E. coli* O157:H7 on Meat Processing Equipment

The effectiveness of the isolated, purified colicins on eliminating *E. coil* O157:H7 from meat processing equipment and other hard surfaces may be examined as follows. A series of aqueous solutions may be prepared with a range of colicin concentrations from about 500 AU/ml to about 1500 AU/ml, and with a series of solutions containing a minor amount of chlorine (household bleach) in a series of concentrations from 0.1 to about 1 ppm. A hard surface, such as a stainless steel mixer or grinder may come in contact with a ground meat that has been pre-contaminated with *E. coli* O157:H7. The surface of the stainless steel plate may be generally wiped off to remove extraneous meat pieces, and the series of colicin solutions sprayed onto defined areas on the surface of the plate to provide a moist coating. After about 5 to about 30 minutes, samples may be separately swabbed from each of the defined areas, plated onto sterile nutrient agar plates, incubated, and examined for growth of *E. coli* O157:H7 colonies. The results would provide a range of effective concentrations of a colicin spray solution for spraying equipment used in meat processing to eliminate growth of *E. coli* O157:H7.

EXAMPLE V

Inhibition of *E. coli* O157:H7 on and in Meat Products

The method described in Example IV for inhibiting *E. coli* O157:H7 on processing equipment, may also be followed to arrive at an effective colicin concentration in a spray which may be applied to the surface of an animal carcass including pieces of meats and ground meats, for eliminating *E. coli* O157:H7. The series of aqueous solutions would be sprayed onto the surface of a series of meat portions as a moist coating. With ground meats, the meat and colicin spray may be mixed together to assess the effectiveness of admixing the colicin throughout the mass.

The meat portions would be stored under refrigeration temperatures (4° C. to 10° C.) to test the effectiveness of the various colicin concentrations over a short term storage (about 1 day to 7 days), and a long term storage (8 days to 3 weeks). Samples of the meat would be periodically be removed and examined for *E. coli* O157:H7 colonies. The results would provide a range of effective concentrations of a sanitizing colicin solution for spraying meats to eliminate growth of *E. coli* O157:H7.

The invention has been described with reference to various specific and preferred embodiments and techniques, and reference to detailed examples wherein the methodologies are as described hereinabove. The examples are not meant to limit the scope of the invention that has been set forth in the foregoing description. It should be understood that many variations and modifications may be made while remaining within the spirit and scope of the invention. The disclosures of the cited references are incorporated by reference herein.

What is claimed is:

1. A method of inhibiting the growth of *Escherichia coli* strain O157:H17, or a variant thereof which retains all of the identifying pathogenic characteristics of strain O157:H7, in an edible non-liquid food substance, comprising:

a) applying a composition consisting essentially of a colicin obtained from a strain of *Escherichia coli* in combination with a carrier to the food substance, in an amount effective to inhibit the growth of said strain O157:H7 or variant thereof, wherein said colicin composition is applied at a substantially neutral to basic pH.

2. The method according to claim 1, wherein the application of the colicin is further effective to also inhibits the growth of a Shigella spp. or Escherichia spp. other than the *E.coli* strain O157:H7 or said variant, in the food substance.

3. The method according to claim 1, wherein the colicin is obtained from a strain of *Escherichia coli* selected from the group consisting of *E. coli* isolate ECL1, *E. coli* isolate ECL6, *E. coli* isolate ECL8, *E. coli* isolate ECL12, and a combination thereof.

4. The method according to claim 1, further comprising, prior to step (a), combining the colicin with an aqueous carrier to form a composition wherein step (a) comprises spraying the composition onto the surface of the food substance.

5. The method according to claim 1, wherein the food substance is an animal carcass or portion thereof, fish, seafood, a ground meat, a beef stick, sausage, bologna, frankfurter, ham, or a combination thereof.

6. The method according to claim 5, wherein the food substance is an animal carcass or portion thereof, and the method further comprises step (b) processing the animal carcass to provide a ground meat with the colicin admixed therethrough.

7. The method according to claim 5, wherein the food substance is a ground meat, and the method further comprises step (b) admixing the colicin with the ground meat.

8. The method according to claim 1, further comprising step (b) maintaining the food substance at a temperature of from about 4° to about 10° C.

9. A method of inhibiting the growth of *Escherichia coli* strain O157:H7, or a variant thereof which retains all of the identifying pathogenic characteristics of strain O157:H7, in an edible non-liquid food substance, comprising:

a) applying a composition consisting essentially of a colicin obtained from a strain of *Escherichia coli* in combination with a carrier and a sanitizing agent to the food substance, in an amount effective to inhibit the growth of said strain O157:H7 or variant thereof, wherein said colicin composition is applied at a substantially neutral to basic pH.

10. A method of inhibiting the growth of *Escherichia coli* strain O157:H7, or a variant thereof which retains all of the identifying pathogenic characteristics of strain O157:H7, on a hard surface, comprising:

a) applying a composition consisting essentially of a colicin obtained from a strain of *Escherichia coli* in combination with a carrier onto the hard surface, in an amount effective to inhibit the growth of said strain O157:H7 or variant thereof.

11. A method of inhibiting the growth of *Escherichia coli* strain O157:H7, or a variant thereof which retains all of the identifying pathogenic characteristics of strain O157:H7, on a hard surface, comprising:

a) applying a composition consisting essentially of a colicin obtained from a strain of *Escherichia* coli in combination with a carrier and a sanitizing agent onto the hard surface, in an amount effective to inhibit the growth of said strain O157:H7 or variant thereof.

* * * * *